United States Patent [19]

Corley

[11] Patent Number: 5,059,572

[45] Date of Patent: Oct. 22, 1991

[54] CATALYST AND PROCESS FOR COUPLING ORGANOMETALLIC REAGENTS WITH ARYL OR VINYLIC HALIDES

[75] Inventor: Larry S. Corley, Houston, Tex.

[73] Assignee: Shell Oil Company

[21] Appl. No.: 429,582

[22] Filed: Oct. 31, 1989

[51] Int. Cl.$^5$ .............................................. B01J 31/24
[52] U.S. Cl. .................................... 502/162; 585/411; 585/469
[58] Field of Search ......................................... 502/162

[56] References Cited

U.S. PATENT DOCUMENTS

| | | | |
|---|---|---|---|
| 4,325,834 | 4/1982 | Bartish et al. | 502/162 X |
| 4,760,194 | 7/1988 | Phillips et al. | 502/162 X |
| 4,822,871 | 4/1989 | Klingensmith | 528/392 |
| 4,822,934 | 4/1989 | Shimizu et al. | 585/25 |

OTHER PUBLICATIONS

Kumada et al., "Phosphine-Nickel Complex Catalyzed Crosscoupling . . . ", *Organic Syntheses* 58, pp. 127-132 (1978).

Kumada, "Nickel and Palladium Complex Cross-Coupling . . . ," *Pure & Appl. Chem.* 52, pp. 669-679 (1980).

*Primary Examiner*—Patrick P. Garvin

[57] ABSTRACT

A process and catalyst are disclosed for the catalyzed reaction of an organometallic reagent with a reactive halide in the presence of a diphosphine complex of a nickel carboxylate or sulfonate. The process can be employed in the synthesis of aromatic compounds such as bisbenzocyclobutenes.

19 Claims, No Drawings

CATALYST AND PROCESS FOR COUPLING ORGANOMETALLIC REAGENTS WITH ARYL OR VINYLIC HALIDES

BACKGROUND OF THE INVENTION

This invention relates to the preparation of aromatic compound a Grignard-type reaction. In a specific aspect, the invention relates to a catalyst for the preparation of bisbenzocyclobutenes.

Bisbenzocyclobutenes are monomers for the preparation of useful homopolymers and copolymers. Certain bisbenzocyclobutenes can be prepared by the reaction of benzocyclobutenyl Grignard reagent with a dihaloarene in the presence of a nickel or palladium catalyst. This type of coupling reaction is generally described, without reference to bisbenzocyclobutenes, in Kumada, *Pure Appl. Chem.* 52. 669–679 (1980).

It is known to use complexes of diphosphines, such as 1,3-bis(diphenylphosphino)propane, with nickel or palladium halides, particularly $NiCl_2$, as catalysts for coupling Grignard reagents or other organometallics (such as organozinc reagents) to aromatic or vinyl halides. Although such diphosphine-nickel halide catalysts work extremely well in some coupling reactions, in others they are prone to "dieout", in which most or all of the catalyst becomes converted into an inactive species early during the reaction and the coupling stops from lack of active catalyst. In other types of reactions (such as Ullmann etherification) in which the "dieout" phenomenon occurs, it can be alleviated by slow addition of the catalyst over a long period of time. This insures that there is always at least a small amount of active catalyst present.

However, with the diphosphine-nickel halide complexes, continuous or incremental addition of the catalyst is difficult because the catalysts are insoluble in solvents, such as ethers, which are compatible with organometallic reagents. The catalysts therefore must be added to the reaction mixture as solids. It is difficult to measure repetitively small portions of solids under an inert atmosphere, especially an atmosphere saturated with solvent vapors. Addition pistons can sometimes be used, as can powder addition funnels using, for example, screw feeders. However, the latter devices tend to clog in atmospheres saturated with solvent vapors as the solid becomes wetted by solvent. Reasonably accurate incremental addition of solids, therefore, is difficult. It would be much more desirable to have a catalyst which is soluble in organometallic-compatible solvents such as ethers or hydrocarbons.

It is therefore an object of the invention to provide a catalyst and process for the reaction of an organometallic reagent and a reactive halide. In one aspect, it is an object of the invention to provide a soluble catalyst for the preparation of a bisbenzocyclobutene.

BRIEF SUMMARY OF THE INVENTION

According to the invention, an aromatic organometallic compound is reacted with a compound containing a reactive aromatic, heteroaromatic or vinylic halide group in the presence of a diphosphine complex of a nickel carboxylate or sulfonate. The catalyst is soluble in tetrahydrofuran and can be added, in solution, incrementally during the Grignard reaction, avoiding the "dieout" problem which can result in low yields. The catalyst has been found particularly useful in the synthesis of bisbenzocyclobutene compounds.

DETAILED DESCRIPTION OF THE INVENTION

The catalyst composition of the invention is a diphosphine complex of a nickel carboxylate or sulfonate. The diphosphine component can be represented by formula (1)

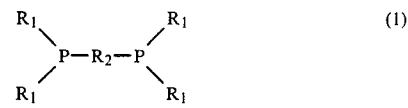

in which each $R_1$ and $R_2$ is independently selected from substituted or unsubstituted $C_{1-20}$ alkyl, aryl, alkaryl, cycloalkyl and heterocyclic radicals. $R_1$ is preferably phenyl. $R_2$ is preferably $C_{2-4}$ alkylene. The preferred diphosphine moiety, because of its availability and the catalytic activity of the resulting complex, is bis(diphenylphosphino)propane, in which each $R_1$ is phenyl and $R_2$ is a propylidene radical.

The preferred nickel carboxylate or sulfonate component can be represented by one of formulas (2) and (3):

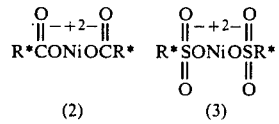

in which each R* is selected independently from hydrogen, $C_{1-24}$, preferably $C_{4-10}$, alkyl, aryl, alkaryl, aralkyl and the like. Examples of such nickel carboxylates include nickel(11) bis(2-ethylhexanoate), nickel formate, nickel acetate, nickel stearate, nickel naphthenate, nickel benzoate, nickel cinnamate, nickel cyclohexanebutyrate, and nickel trifluoroacetate. The two carboxyl groups may also be part of the same acid molecule as in nickel dodecenyl succinate. Examples of nickel sulfonates include nickel benzenesulfonate, nickel bis(dodecylbenzenesulfonate), nickel hexadecanesulfonate, nickel naphthalenesulfonate, and the like, and the two sulfonate groups may also be part of the same acid molecule. The preferred nickel catalyst component, because of its availability and demonstrated catalytic activity, is nickel(II) bis(2-ethyl hexanoate).

The catalytic complex can be prepared by contacting the phosphine component and the nickel component in a suitable liquid medium. Preparation and storage of the resulting solution are carried out in the absence of oxygen. The nickel component will generally be added to a solution of the phosphine component in an amount of about 0.8:1 to about 1.5:1 moles per mole of the phosphine component. The preferred solvent for preparation of the catalyst is tetrahydrofuran.

The reactions of interest involve the formation of an organometallic reagent such as a hydrocarbyl magnesium halide (a Grignard reagent) and the subsequent reaction of the organometallic reagent with a reactive group-containing compound according to the generalized (unbalanced) formula (2)

in which R is an unsubstituted or non-interfering substituted aliphatic, aromatic or heterocyclic radical; M is an alkali or alkaline earth metal, boron, aluminum, zinc or cadmium; R' is an aromatic, heteroaromatic or vinyl group; and Y is a halide or sulfonate.

The invention process is an application of such organometallic coupling reactions, catalyzed by the above-described diphosphine complex of a nickel carboxylate or sulfonate. The process can be described by the general formula (3)

$$c\ R_aMX_b + a\ R'Y_c \rightarrow a\ (R)_cR' + c\ MX_bY_a \quad (3)$$

in which R is an unsubstituted or non-interfering substituted aromatic radical, preferably cyclobutenoaryl, most preferably benzocyclobutenyl; R' is an unsubstituted or non-interfering substituted aromatic, heteroaromatic or vinylic group; M is selected from alkali metals, alkaline earth metals, boron, aluminum, zinc and cadmium; a is an integer of at least one; (a+b) equals the valence of M; c is 1, 2 or 3; and X and Y independently are selected from chlorine, bromine and iodine. Non-interfering substituents include, for example, alkyl, aryl, ether, thioether, cycloalkyl and heterocyclic.

Synthesis of a desired product according to the invention process involves contacting an aromatic organometallic reagent and an aromatic, heteroaromatic or vinylic halide in the presence of the invention catalytic complex. The organometallic reagent is generally formed by the reaction of a metal, such as magnesium, with a halogenated aromatic compound (or with the aromatic compound in the case, for example, of lithium metal). The reaction is carried out in a suitable solvent such as tetrahydrofuran, under an inert atmosphere such as nitrogen. The temperature of the exothermic reaction is generally maintained below about 45° C.

The resulting Grignard or other organometallic reagent is reacted with a compound halogenated at linking site(s) to produce the intended product. The reaction is carried out at a temperature effective to maintain the organometallic reagent in solution but not so high as to boil off the solvent, generally within the range of about 35° to about 45° C.

In a preferred embodiment of the invention process, a bisbenzocyclobutene is prepared by the reaction of a benzocyclobutenylmetallic compound, such as benzocyclobutenylmagnesium halide, with a reactive aromatic, heteroaromatic or vinylic halide in the presence of a diphosphine complex of a nickel carboxylate or sulfonate. For example,

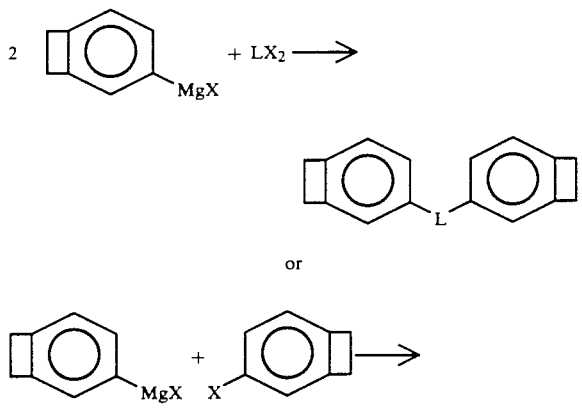

The generalized reaction can thus be represented by the formula (4)

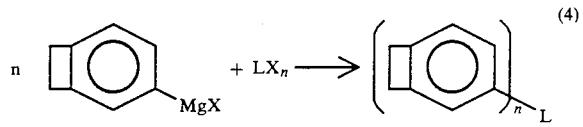

where X is chlorine, bromine or iodine; L is an unsubstituted or noninterfering substituted aromatic, vinylic or heteroaromatic group; and n is 1, 2 or 3. Examples of L include phenylene, naphthalenediyl, pyridinediyl, quinolinediyl, dibenzofurandiyl, thiophenediyl, vinylene, phenylenebis(vinylene), naphthylenebis(methylvinylene), and the like.

The reaction is carried out in the presence of the nickel catalyst as described above. The catalyst will be present in the reaction solution in an amount effective to promote the reaction of the Grignard or other organometallic reagent with the halogenated compound, generally within the range of about 0.001 to about 0.1 moles of catalyst per mole of the organometallic reagent. The exothermic reaction can generally be carried out without added heat, and the reaction mixture should generally be maintained below about 45° C. The reaction time will vary depending upon the reactants and other reaction conditions but will generally be at least about 1 hour, usually within the range of about 2 to about 15 hours. The most efficient reaction will be possible with incremental addition of the catalyst over at least the initial period of reaction. For example, an initial increment of catalyst can be used to initiate the reaction, with increments added in selected portions after each 2 hours of the reaction. A schedule of incremental catalyst additions alleviates the effects of "die-out" of the catalyst during the course of the reaction.

After completion of the reaction, a small amount of water can be added to consume any excess Grignard reagent. The solvent and unconsumed reactants can be removed by suitable means such as distillation, and the desired product can be separated from unwanted by-products by suitable means such as solvent extraction. A specific embodiment of the invention process is illustrated in the following examples.

EXAMPLE 1

This comparative example illustrates the preparation of a bisbenzocyclobutene compound, 4,4'-(1,3-phenylene)bisbenzocyclobutene, from 4-benzocyclobutenyl Grignard reagent and 1,3-dichlorobenzene using addition of a powdered diphosphine-nickel chloride complex catalyst in one portion. A 4-neck 250-mL flask was fitted with a magnetic stirring bar, a thermometer, a septum, a condenser and two addition funnels. (All glassware was dried at 125° C. overnight, or at 140° C. for 2 hours, before use. To the flask was added 1.5422 grams 0.06343 moles) of magnesium turnings. Into one addition funnel was poured 11.06 grams (0.06042 moles) of 4-bromobenzocyclobutene (previously dried over calcium chloride). To the other addition funnel was added 30 grams of dry tetrahydrofuran (THF). The system was purged with dry nitrogen, and the 4-bromobenzocyclobutene and THF were slowly added, with stirring, from the addition funnels to the flask. A cold water bath was used, as needed, to keep the reaction temperature below approximately 45° C. The system was allowed to react for about 4 hours to allow relatively complete transformation of the 4-bromobenzocyclobutene into the Grignard reagent. At the end of this period, the mixture was a milky white dispersion of precipitated benzocyclobutenyl Grignard reagent.

A second 250-mL flask was fitted with a magnetic stirring bar, a thermometer, a septum, and a condenser. To the flask were added 0.1562 grams (0.0002881 moles) of 1,3-bis(diphenylphosphino)propanenickel(II) chloride and 3.70 grams (0.0252 moles) of I,3-dichlorobenzene. The flask was purged with nitrogen. Then, the Grignard reagent mixture in the first flask was warmed to 35–40° C. to bring the precipitated Grignard reagent into solution. The Grignard solution was then transferred to the second flask with a syringe. Upon the addition of the Grignard solution, the powdered nickel complex was converted into a soluble species and went into solution. Immediately after the addition of the Grignard reagent solution, the flask temperature was 31.5° C. It rose to 37° C. after 10 minutes and stayed at this level for about 15 minutes. When the temperature began to decline, heat was applied, bringing the solution temperature to 72° C. after 15 minutes of heating. Heating was then removed and the mixture was allowed to cool to room temperature, at which temperature it was stirred overnight.

The following morning, a small amount of water was added to the reaction mixture to consume any excess Grignard reagent. THF was then distilled off at atmospheric pressure, and benzocyclobutene and unreacted 1,3-dichlorobenzene were removed by steam distillation. The organic phase was then dissolved in cyclohexane, and the cyclohexane layer was extracted with 25 mL of 30% aqueous sulfuric acid and then with water. Cyclohexane was then removed on a rotary evaporator under vacuum. The crude yield of product was 2.72 grams (38.3%). Results of additional experiments of this type are shown in Table 1. One can see from the results in Table 1 that reaction yields tend to be highly irreproducible, most likely because of catalyst "dieout" during the reaction.

EXAMPLE 2

This example illustrates the preparation of the same compound as in Example 1 but with incremental addition of a THF solution of a diphosphine-nickel 2-ethylhexanoate complex catalyst. A commercially available solution of nickel(II) bis(2-ethylhexanoate) in paraffin oil, containing 12% Ni (0.9621 g, 0.001966 moles Ni) was dissolved in 90.0 grams (101.6 mL) of THF. 1,3-Bis(diphenylphosphino)propane (0.8307 g, 0.002014 moles) was added and the resultant complex (in contrast to the behavior of the corresponding chloride) stayed in solution. The solution was sparged for approximately 30 minutes with dry nitrogen (to remove traces of atmospheric oxygen) and then stored in a flask topped with a stopcock.

As in Example 1, a 4-neck 250-mL flask was fitted with a magnetic stirring bar, a thermometer, a septum, a condenser and two addition funnels. (All glassware was dried at 125° C. overnight, or at 140° C. for 2 hours, before use.) To the flask was added 1.5498 grams (0.06375 moles) of magnesium turnings. Into one addition funnel was poured 11.06 grams (0.06042 moles) of 4-bromobenzocyclobutene (previously dried over calcium chloride). To the other addition funnel was added 40 grams of dry tetrahydrofuran (THF). The system was purged with dry nitrogen and the 4-bromobenzocyclobutene and THF were slowly added with stirring, from the addition funnels to the flask. A cold water bath was used, as needed, to keep the reaction temperature below approximately 45° C. The system was allowed to react for approximately 4 hours to allow transformation of the 4-bromobenzocyclobutene into the Grignard reagent. At the end of this period, as in Example 1, the mixture was a milky white dispersion of precipitated benzocyclobutenyl Grignard reagent.

A second 250.mL flask was fitted with a magnetic stirring bar, an addition funnel, a thermometer, a septum, and a condenser. To the flask was added 3.70 grams (0.0252 moles) of I,3-dichlorobenzene. To the addition funnel was added 10 mL of the above 1,3-bis(diphenylphosphino)propanenickel(II) bis(2-ethylhexanoate) solution. The flask was purged with nitrogen. Then, the Grignard reagent mixture in the first flask was warmed to 35–40° C. to bring the precipitated Grignard reagent into solution. The Grignard solution was then transferred to the second flask with a syringe. Immediately after the addition of the Grignard reagent solution, the flask temperature was 31.5° C. It rose to 32° C. two minutes after addition of the first portion (4 mL) of the catalyst solution. The temperature then began to decline slowly. Another 2 mL portion of catalyst solution was added after 1.5 hours, another 2 mL after 3.2 hours, and the final 2 mL after 4.6 hours. The temperature rose by about 1° C. after each catalyst addition and then started to decline. After the addition of the final portion of catalyst, the mixture was allowed to stand overnight to complete the reaction.

The following morning, a small amount of water was added to the reaction mixture to consume any excess Grignard reagent. THF was then distilled off at atmospheric pressure, and benzocyclobutene and unreacted 1,3-dichlorobenzene were removed by steam distillation. The organic phase was then dissolved in cyclohexane and the cyclohexane layer was extracted with 30% aqueous sulfuric acid and then with water. Cyclohexane was then removed on a rotary evaporator under vacuum. The crude yield of product was 5.84 grams (82.1%). The liquid chromatographic scan of the product was similar to that of the product of Example 1. Results of additional experiments of this type are shown in Table 2. One can see from the results in Table 2 that crude reaction yields tend to be high and quite reproducible.

TABLE 1

Synthesis of 4,4'-(1,3-phenylene)bisbenzocyclobutene

| Expt. # | Scale (moles Mg) | Molar ratios used BrBCB Mg | DCB Mg | Ni Mg | THF Mg | Temperature during coupling phase | | Crude yield, % | Crude product HPLC peaks[a] (retention times in minutes) 35.5–36.6 | 36.4–38.0 | 43.5–45.2 | 48.3–52.0 |
| --- | --- | --- | --- | --- | --- | --- | --- | --- | --- | --- | --- | --- |
| 1 | 0.06 | 0.998 | 0.414 | 0.00147 | 13.8 | Start: 5° C. | | 70.5 | 14.63 | 5.46 | 70.4 | 2.26 |
| 2 | 0.61 | 0.999 | 0.416 | 0.00145 | 11.7 | Start: 5° C. | | 24.1 | | | | |
| 3 | 0.06 | 0.949 | 0.395 | 0.00130 | 13.1 | Start: 5° C. | | 30.4 | 14.85 | 25.35 | 41.54 | 7.96 |
| 4 | 0.06 | 0.951 | 0.396 | 0.00123 | 13.1 | Start: 10° C. | 40° C. exotherm | 23.1 | 11.48 | 23.18 | 46.38 | 8.03 |
| 5 | 0.06 | 0.953 | 0.397 | 0.00443 | 13.1 | Start: RT | 50° C. exotherm | 65.0 | 7.59 | 8.41 | 75.10 | 4.27 |
| 6 | 0.06 | 0.949 | 0.395 | 0.00324 | 13.1 | Start: 23° C. | 1° C. exotherm | 65.7 | 17.16 | 16.44 | 51.45 | 6.79 |
| 7 | 0.06 | 0.949 | 0.395 | 0.00225 | 13.1 | Start: 23° C. | no exotherm seen | 9.8 | 14.61 | 24.60 | 45.60 | 3.85 |
| 8 | 0.06 | 0.952 | 0.397 | 0.00454 | 6.6 | Start: 26° C. | 5.5° C. exotherm | 38.3 | 13.09 | 17.38 | 53.68 | 5.48 |

[a]HPLC peak area % by UV detection at 280 nm (may not represent actual weight or mole fractions of components). The peak at 36.4–38.0 minutes is 4,4'-bisbenzocyclobutenyl, while the peak at 43.5–45.2 minutes is 4,4'-(1,3-phenylene)bisbenzocyclobutene.

TABLE 2

Synthesis of 4,4'-(1,3-phenylene)bisbenzocyclobutene

| Expt. # | Scale (moles Mg) | Molar ratios used BrBCB Mg | DCB Mg | Ni Mg | THF/Mg Initial | Final | Elapsed time (hours)- % of catalyst added | Crude yield, % | Crude product HPLC peaks[b] (retention times in minutes) 35.5–36.6 | 36.4–38.0 | 43.5–45.2 | 48.3–52.0 |
| --- | --- | --- | --- | --- | --- | --- | --- | --- | --- | --- | --- | --- |
| 1 | 0.06 | 0.952 | 0.397 | 0.00335 | 8.7 | 10.9 | 0–64, 1–18, 2.15–18 | 87.8 | 14.10 | 16.99 | 47.67 | 9.98 |
| 2 | 0.06 | 0.948 | 0.395 | 0.00304 | 8.7 | 10.6 | 0–40, 1.5–20, 3.2–20, 4.6–20 | 82.1 | 13.79 | 18.25 | 45.94 | 9.50 |
| 3 | 0.25 | 0.952 | 0.397 | 0.00338 | 8.7 | 10.9 | 0–25, 1.7–9, 5.25–11, 9–11, 23–11, 26.4–11, 29.5–11, 31.2–11 | 74.2 | 5.79 | 16.92 | 42.76 | 14.51 |
| 4 | 1.14 | 0.942 | 0.397 | 0.00171 | 8.7 | 9.8 | 0–20, 4.3–10, 22–20, 27.5–20, 30.75–30 | 86.6 | | | | |

[a]In experiments #2 and earlier, the Grignard reagent solution was transferred by syringe (or double-tipped needle) to a flask which contained 1,3-dichlorobenzene. In experiments #3 and later, the dichlorobenzene was added to the Grignard reagent solution in the flask in which the Grignard solution was prepared.
[b]Peak identification same as in footnote [a] of Table 1.

I claim:

1. A composition comprising a chemical complex formed by contacting, in a liquid medium,
(a) a diphosphine of the formula

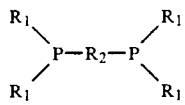

in which each $R_1$ and $R_2$ are selected independently from $C_{1-20}$ alkyl, aryl, alkaryl and aralkyl, and
(b) a nickel (II) carboxylate or sulfonate.

2. The composition of claim 1 in which the nickel (II) carboxylate can be represented by the formula Ni(CO$_2$R*)$_2$, in which each R* is selected from $C_{1-24}$ alkyl, aryl, alkaryl and aralkyl.

3. The composition of claim 1 in which the nickel (II) sulfonate can be represented by the formula Ni(SO, in which each R is selected from $C_{1-24}$ alkyl, aryl, alkaryl and aralkyl.

4. The composition of claim 2 in which each R* is selected from $C_{4-10}$ alkyl.

5. The composition of claim 3 in which each R* is selected from $C_{4-10}$ alkyl.

6. The composition of claim 1 in which each $R_1$ is phenyl and $R_2$ is selected from $C_{2-4}$ alkylene.

7. The composition of claim 1 in which $R_2$ is —(CH$_2$)$_3$—.

8. The composition of claim which further comprises tetrahydrofuran.

9. The composition of claim 7 in which the nickel(II) carboxylate is nickel(II) bis(2-ethyl hexanoate).

10. The composition of claim 3 in which the nickel(II) sulfonate is nickel(II) bis(dodecylbenzene sulfonate).

11. A process for preparing a catalyst comprising contacting, in a liquid medium at a temperature within the range of about −25° to about 100° C., (a) a diphosphine of the formula

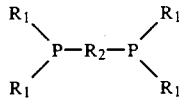

in which each $R_1$ and $R_2$ is selected independently from divalent $C_{1-20}$ alkyl, aryl, alkaryl and aralkyl (b) a nickel(II) carboxylate or sulfonate.

12. The process of claim 11 in which the nickel (II) carboxylate can be represented by the formula Ni(CO$_2$R*)$_2$, in which each R* is selected from $C_{1-24}$ alkyl, aryl, alkaryl and aralkyl.

13. The process of claim 11 in which the nickel (II) sulfonate can be represented by the formula Ni(SO$_3$R*)$_2$, in which each R* is selected from $C_{1-24}$ alkyl, aryl, alkaryl and aralkyl.

14. The process of claim 12 in which R* is selected from $C_{4-10}$ alkyl.

15. The process of claim 13 in which R* is selected from $C_{4-10}$ alkyl.

16. The process of claim 11 in which each $R_1$ is phenyl and $R_2$ is $C_{2-4}$ alkylene.

17. The process of claim 11 in which $R_2$ is —(CH$_2$)$_3$—.

18. The process of claim 12 in which the nickel(II) carboxylate is nickel(II) bis(2-ethylhexanoate).

19. The process of claim 13 in which the nickel(II) sulfonate is nickel(II) bis(dodecylbenzenesulfonate).

* * * * *